US011464274B2

(12) United States Patent
Roh et al.

(10) Patent No.: US 11,464,274 B2
(45) Date of Patent: Oct. 11, 2022

(54) INSOLE AND SHOES COMPRISING THE SAME

(71) Applicant: Samsung Electronics Co., Ltd., Suwon-si (KR)

(72) Inventors: Se-Gon Roh, Suwon-si (KR); Haewook Ahn, Seoul (KR); Yeji Bae, Seoul (KR); Minho Choi, Seoul (KR); Chang Hyun Roh, Seongnam-si (KR); Youngbo Shim, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 223 days.

(21) Appl. No.: 16/661,338

(22) Filed: Oct. 23, 2019

(65) Prior Publication Data

US 2020/0281303 A1 Sep. 10, 2020

(30) Foreign Application Priority Data

Mar. 5, 2019 (KR) ........................ 10-2019-0025343

(51) Int. Cl.
*A43B 3/00* (2022.01)
*A43B 17/18* (2006.01)
*A43B 3/34* (2022.01)

(52) U.S. Cl.
CPC ................ *A43B 3/34* (2022.01); *A43B 17/18* (2013.01)

(58) Field of Classification Search
CPC .................................................. A43B 3/0005
See application file for complete search history.

(56) References Cited

U.S. PATENT DOCUMENTS

| 5,592,759 | A | * | 1/1997 | Cox ...................... A43B 1/0054 36/136 |
| 5,846,063 | A | * | 12/1998 | Lakic ................... A43B 13/203 417/440 |
| 6,195,921 | B1 | * | 3/2001 | Truong .................... A43B 3/00 340/573.1 |
| 7,347,831 | B2 | * | 3/2008 | Chiu ........................ A43B 3/35 36/2.6 |
| 7,997,007 | B2 | * | 8/2011 | Sanabria-Hernandez ................... A43B 3/36 36/137 |
| 8,308,665 | B2 | | 11/2012 | Harry et al. |
| 8,398,570 | B2 | | 3/2013 | Mortimer et al. |
| 2002/0133973 | A1 | * | 9/2002 | Lin ...................... A41B 11/007 36/2.6 |

(Continued)

FOREIGN PATENT DOCUMENTS

EP    1608303 A2    12/2005
EP    2 675 355 A2    12/2013

(Continued)

OTHER PUBLICATIONS

Extended European Search Report dated Jun. 29, 2020 for the corresponding EP Application No. 19214921.9.

*Primary Examiner* — Jila M Mohandesi
(74) *Attorney, Agent, or Firm* — Harness, Dickey & Pierce, P.L.C.

(57) ABSTRACT

An insole including a base; an electronic element provided to the base; a connection line configured to extend from the electronic element and to pass through the base; and a cover provided on a top surface of the base to cover the electronic element and configured to be separable from the base.

14 Claims, 11 Drawing Sheets

(56) References Cited

U.S. PATENT DOCUMENTS

| | | | |
|---|---|---|---|
| 2006/0248749 A1* | 11/2006 | Ellis | A43B 13/181 36/28 |
| 2009/0019725 A1* | 1/2009 | Wang | A43B 3/34 36/1 |
| 2011/0107771 A1 | 5/2011 | Crist et al. | |
| 2011/0214501 A1* | 9/2011 | Ross | A61B 5/6807 73/172 |
| 2011/0251520 A1 | 10/2011 | Shieh et al. | |
| 2017/0112712 A1 | 4/2017 | Chawan et al. | |
| 2018/0042338 A1* | 2/2018 | Orand | A43B 13/184 |
| 2018/0055140 A1 | 3/2018 | Antonetti et al. | |
| 2018/0085030 A1 | 3/2018 | Krimmer et al. | |

FOREIGN PATENT DOCUMENTS

| | | |
|---|---|---|
| EP | 3 153 046 A1 | 4/2017 |
| IN | 230069 | 9/2007 |
| JP | 4988942 B1 | 8/2012 |
| KR | 100795830 B1 | 1/2008 |
| KR | 101115495 B1 | 3/2012 |
| KR | 101878254 B1 | 7/2018 |
| KR | 10-2020-0023879 | 3/2020 |

* cited by examiner

INSOLE AND SHOES COMPRISING THE SAME

CROSS-REFERENCE TO RELATED APPLICATION

This application claims priority under 35 U.S.C. § 119 to Korean Patent Application No. 10-2019-0025343, filed on Mar. 5, 2019, in the Korean Intellectual Property Office, the entire contents of which are incorporated herein by reference in their entirety.

BACKGROUND

1. Field

Some example embodiments relate to an insole and/or shoes including the insole.

2. Description of the Related Art

A user wears shoes in daily life. Shoes protect feet of the user comfortably and safely. In recent years, wearable devices are developed to detect a gait pattern of the user and to assist the user to stably walk by providing a sensor and/or a driver to a shoe.

SUMMARY

Some example embodiments relate to an insole.

In some example embodiment, the insole includes a base; an electronic element including a connection line, the electronic element insertable in the base such that the connection line extends from the electronic element and passes through the base; and a cover configured to detachably connect to a top surface of the base such that the cover covers the electronic element when the cover is connected to the base.

In some example embodiment, the base includes a base body configured to support the electronic element; and a base protrusion protruding from the base body, the base protrusion configured to connect to the cover such that the electronic element supported by the base body is surrounded by the base protrusion.

In some example embodiment, the electronic element includes at least one electronic device; and a support layer configured to support the at least one electronic device and the connection line.

In some example embodiment, the base body has a base hole passing therethrough such that a front sidewall of the base hole is sloped rearward and downward from the base body to form a guide.

In some example embodiment, the support layer includes a layer body configured to rest on the top surface of the base, the connection line extending along a top surface of the layer body; and a ramp formed on a central portion of the layer body, the ramp having a slope corresponding to a slope of the guide such that, when the electronic element is inserted into the base, the connection line runs along the ramp and passes through the base.

In some example embodiment, the at least one electronic device includes a plurality of electronic devices including, a front electronic device configured to overlap a forefoot of a user based on a direction perpendicular to the base; and a rear electronic device configured to overlap a rear foot of the user based on the direction perpendicular to the base.

In some example embodiment, when the electronic element is inserted into the base, the base hole in the base body is at a position corresponding to a location between the front electronic device and the rear electronic device.

In some example embodiment, the cover includes a cover body including a cover groove configured to receive the base protrusion; and a cover protrusion configured to protrude from the cover body and to press against the support layer of the electronic element.

In some example embodiment, the insole further includes a controller insertable into the base such that, when the electronic element is inserted into the base, a surface of the controller faces the electronic element.

In some example embodiment, the controller includes a controller body having a controller protrusion extending rearward from the controller body, such that the controller is insertable into the base by inserting the controller in a main groove in the base such that the controller protrusion penetrates an auxiliary groove within the main groove, the auxiliary groove extending in a direction perpendicular to the base.

In some example embodiment, the base further includes an insert in the main groove, the insert including a more rigid material than that of the base, wherein the controller and the insert are configured to be combinable in a state in which the connection line is between the controller and the insert.

In some example embodiment, the electronic element includes at least one electronic device including a vibrator, a pressure sensor, a temperature sensor, or an inertial sensor.

Some example embodiments relate to a shoe.

In some example embodiment, the shoe includes a midsole; an upper on a top surface of the midsole; and an insole including, a base insertable into the upper, an electronic element including a connection line, the electronic element insertable in the base such that the connection line extends from the electronic element and passes through the base, and a cover configured to detachably connect to a top surface of the base such that the cover covers the electronic element when the cover is connected to the base.

In some example embodiment, the insole further includes a controller insertable into the base such that, when the electronic element is inserted into the base, the controller is connected to the connection line.

In some example embodiment, the shoe further includes an interface attached to an exterior of one of the upper and the midsole, the interface configured to connect to the controller.

In some example embodiment, the interface includes an interface body configured to fasten to the midsole; an interface cover including a power terminal, the interface cover detachably connected to the interface body; and a connector configured to pass through the upper and connect the power terminal to the controller.

In some example embodiment, the interface body includes a body magnet having a first polarity, and the interface cover further includes a cover magnet configured to face the body magnet, the cover magnet having a second polarity opposite the first polarity.

In some example embodiment, the base includes a base body configured to support the electronic element; and a base protrusion protruding from the base body, the base protrusion configured to connect to the cover such that the electronic element supported by the base body is surrounded by the base protrusion.

In some example embodiment, the midsole includes a midsole body configured to support the insole, the midsole body including a plurality of midsole grooves recessed in front portion of a top surface thereof and extending in a direction intersecting a longitudinal direction of the midsole body such that, when the electronic element is inserted into the base, the plurality of midsole grooves are in front of an electronic device associated therewith.

Some example embodiments relate to a shoe,

In some example embodiment, the shoe includes a midsole; an upper on a top surface of the midsole; and an insole including, a base insertable into the upper, a controller insertable into the base, and an electronic element including a connection line, the connection line configured to connect the electronic element to the controller.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
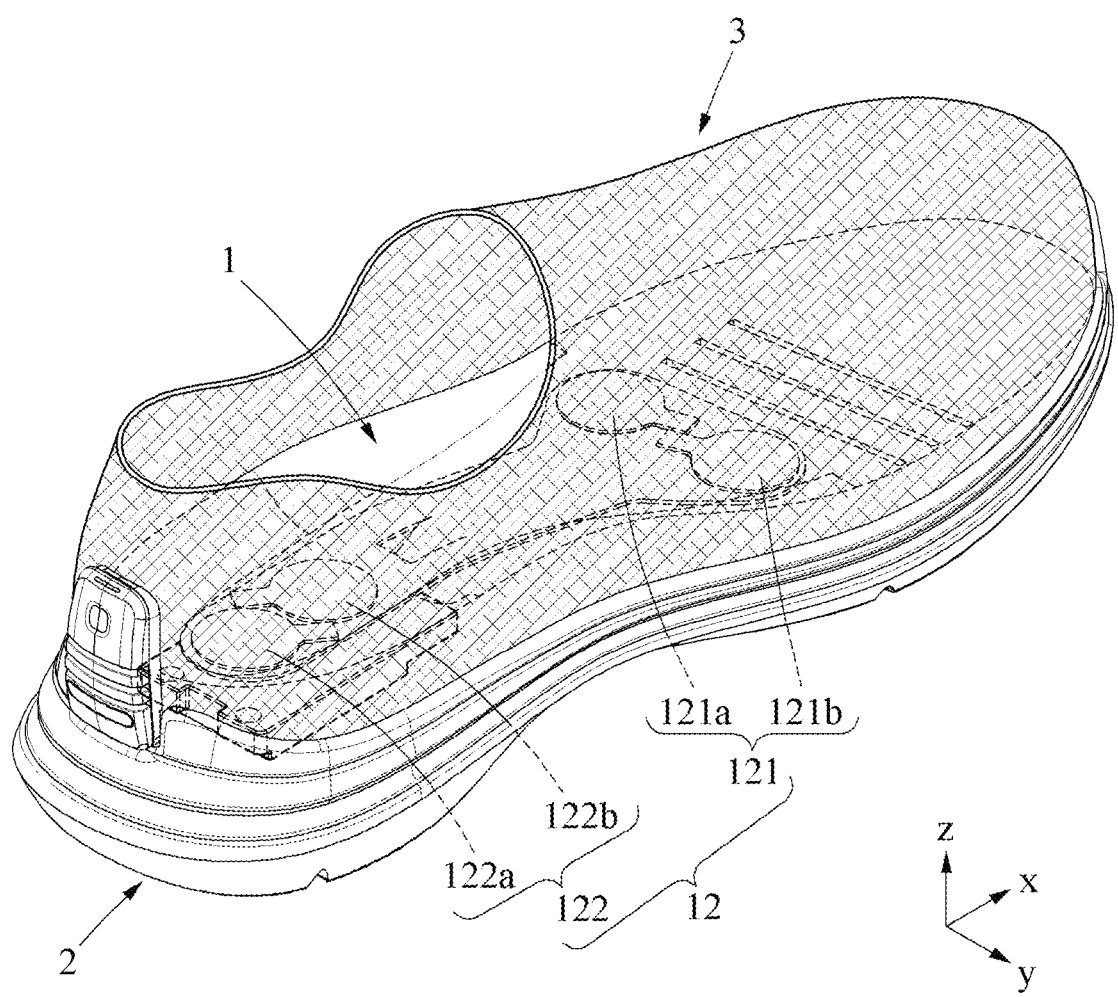
FIG. 1 is a perspective view of a shoe according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit example embodiments to the particular example embodiments disclosed herein. On the contrary, the example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
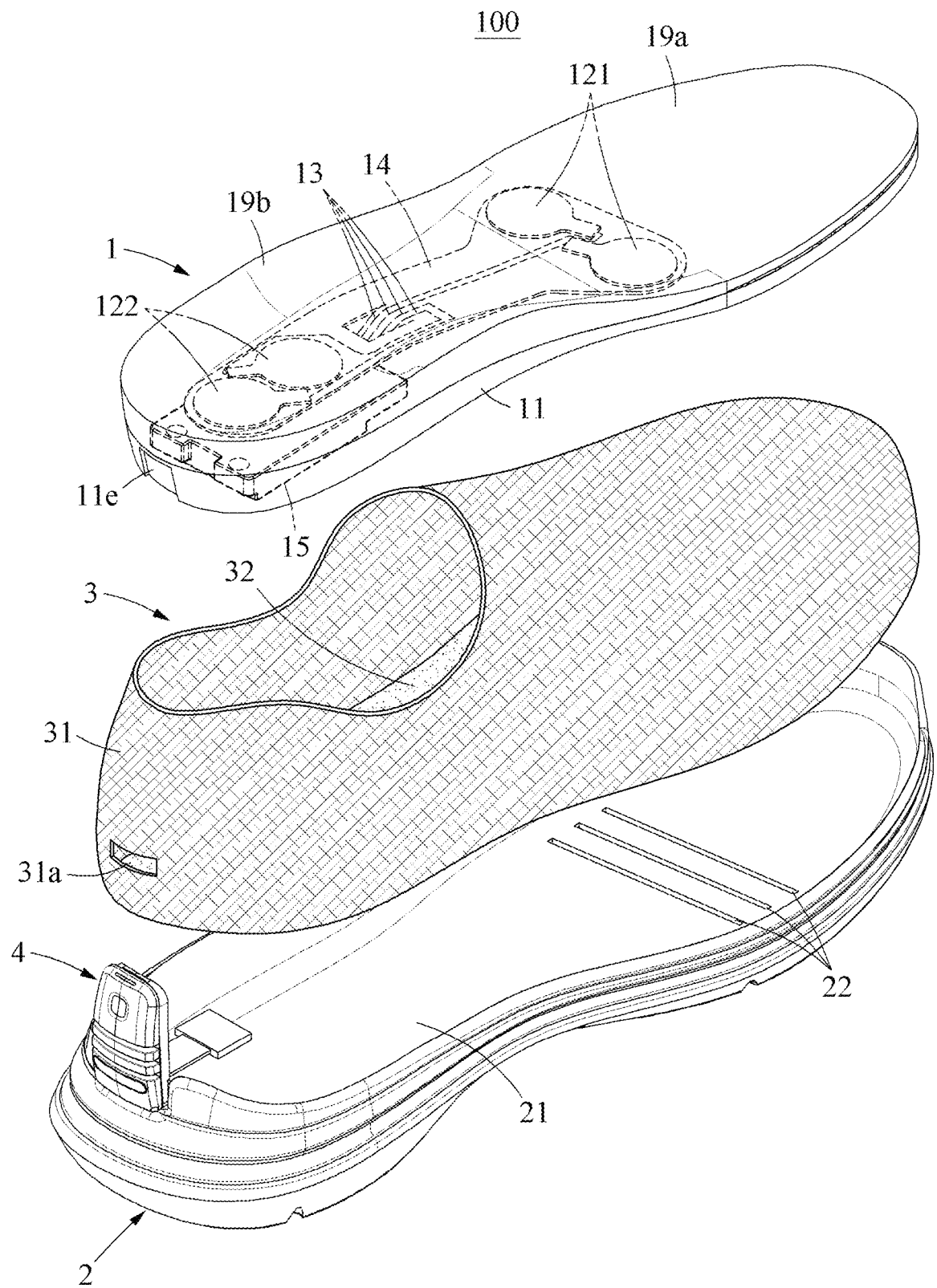
FIG. 2 is an exploded perspective view of a shoe according to at least one example embodiment.
Figure 3:
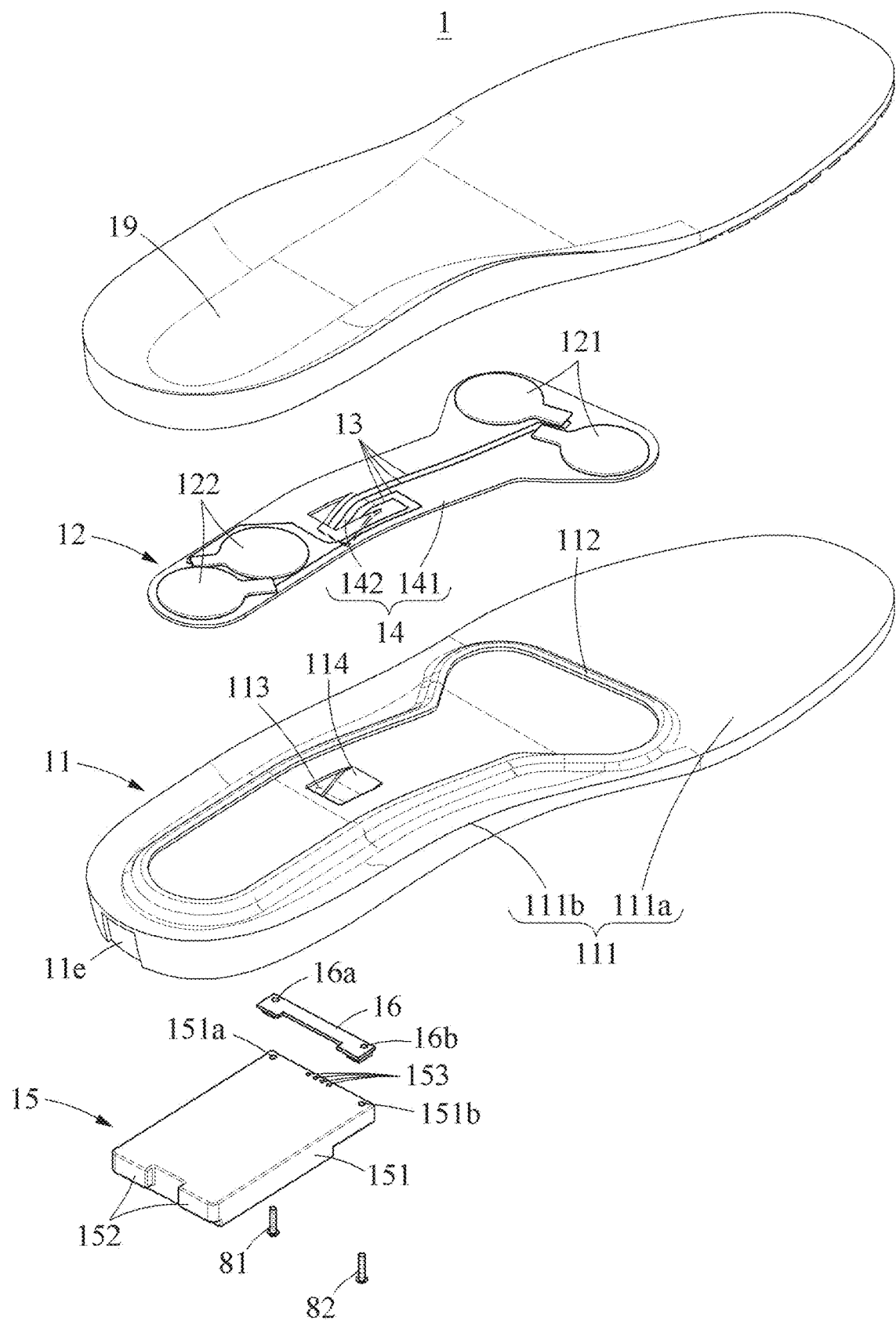
FIG. 3 is an exploded perspective view of an insole according to at least one example embodiment.
Figure 4:
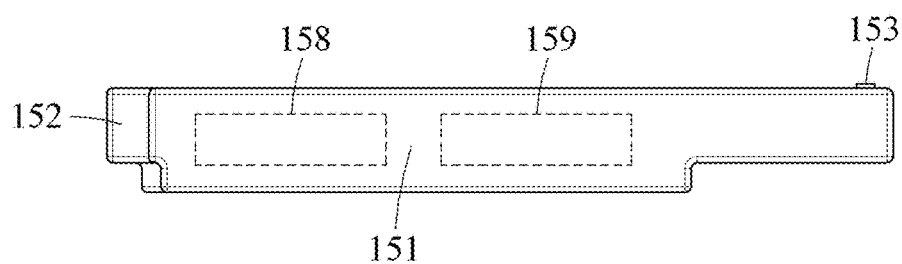
FIG. 4 is a side view of a controller according to at least one example embodiment.

FIG. 1 is a perspective view of a shoe according to at least one example embodiment, FIG. 2 is an exploded perspective view of a shoe according to at least one example embodiment, FIG. 3 is an exploded perspective view of an insole according to at least one example embodiment, and FIG. 4 is a side view of a controller according to at least one example embodiment.

Referring to FIGS. 1 to 4, a shoe 100 may include an insole 1, a midsole 2, an upper 3, and an interface 4.

The shoe 100 may apply stimuli to a foot of a user or may measure a movement of the foot of the user using an electronic element 12 included in the insole 1. The electronic element 12 may include a front electronic element 121 configured to overlap a forefoot of the user based on a direction perpendicular to the insole 1 and a rear electronic element 122 configured to overlap a rearfoot of the user based on the direction perpendicular to the insole 1. Here, the direction perpendicular to the insole 1 refers to a direction perpendicular to a top surface of the insole 1, that is, a surface of the insole 1 that contacts a sole of the user, and indicates an approximately z-axial direction based on coordinate axes of FIG. 1. A longitudinal direction of the insole 1 indicates an approximately x-axial direction based on coordinate axes of FIG. 1. Unless described otherwise, a "front portion" indicates a +x-axial direction and a "rear portion" indicates a −x-axial direction in a coordinate system of FIG. 1.

The insole 1 includes a surface that contacts the sole of the user and may support the foot of the user. The insole 1 may be formed of a flexible material and may give an enhanced comfort when the user wears the shoe 100. The insole 1 may be inserted inward into the upper 3 through an upper opening of the upper 3. The insole 1 may be provided on an upper sole 32 of the upper 3. For example, when the upper 3 does not include the upper sole 32, the insole 1 may be directly provided on a top surface of the midsole 2. For example, the insole 1 may be separable from the upper 3.

The insole 1 may include a base 11, the electronic element 12, a connection line 13, a support layer 14, a controller 15, an insert 16, a cover 19, and coupling members 81 and 82.

The base 11 and the cover 19 may couple with each other or may be separable from each other. The user may clean and/or replace the cover 19 by separating the cover 19 from the base 11. All of electronic components, for example, the electronic element 12 and the controller 15, included in the insole 1 may be provided to the base 11, and none of the components may be provided to the cover 19. The cover 19 may make a direct contact with the sole of the user and thus, may be relatively easily contaminated compared to the base 11 that does not make a direct contact with the sole of the user. The user may maintain the shoe 100 to be in an excellent hygienic state by separating and cleaning only the cover 19.

The base 11 may be in a shape corresponding to an inner space of the upper 3. For example, the base 11 may insert inward into the upper 3 through a portion open in an upper portion of the upper 3. The base 11 may include a base body 111, a base protrusion 112, a base hole 113, and a guide 114.

The base body 111 may support the electronic element 12. The front electronic element 121 may be provided in a front portion of the base body 111, and the rear electronic element 122 may be provided in a rear portion of the base body 111. The base body 111 may include a base sole 111a configured to support the sole of the user and a base wing 111b configured to protrude upward from a rear edge of the base sole 111a. The base wing 11b may surround at least a portion of an edge of the cover 19 that is placed on a top surface of the base body 111 and may inhibit (or, alternatively, prevent) the cover 19 from being pushed rearward in a −x-axial direction or being shaken in a y-axial direction.

The base protrusion 112 may protrude from the base body 111 and may be inserted into the cover 19. For example, the base protrusion 112 may be fitted to the cover 19. Here, fit may include a tight fit scheme and a scheme of a mutual geometric coupling method to reduce sliding of the cover 19 relative to the base 11. The cover 19 may include a cover groove that is recessed from a bottom surface of the cover 19, and the base protrusion 112 may insert into the cover groove. The base protrusion 112 may inhibit (or, alternatively, prevent) the cover 19 from being shaken in a horizontal direction, for example, an x-axial direction or a y-axial direction. The base protrusion 112 may surround the electronic element 12. For example, the base protrusion 112 may be in a shape that surrounds all of the front electronic element 121 and the rear electronic element 122. Although the base protrusion 112 is in a shape of a closed curve, it is provided as an example only. For example, the base protrusion 112 may be in a segmented shape including a plurality of unit bodies.

The base hole 113 may be formed to pass through the base body 111. The base hole 113 may be formed in a direction perpendicular to the insole 1, that is, a z-axial direction. The base hole 113 may serve as a path that guides the connection line 13 from the top surface to a bottom surface of the base 11. The connection line 13 may pass through the base hole 113 and may be connected to the controller 15. According to the structure as above, the electronic element 12 that interacts with the foot of the user may be provided to be in close contact with the foot of the user and an effect of pressure triggered by the foot of the user against the controller 15 may be reduced, which may lead to enhancing durability of the controller 15.

The base hole 113 may be formed between the front electronic element 121 and the rear electronic element 122. That is, the base hole 113 may be formed in a portion that overlaps a midfoot portion. According to the above structure, while the user is walking, pressure applied to the base hole 113 and the connection line 13 passing the base hole 113 may relatively decrease, which may lead to reducing a disconnection risk of the connection line 13. For example, during the progress of push-off, strong pressure may be applied to a portion that overlaps a forefoot portion in the insole 1, that is, a portion to which the front electronic element 121 is provided. Likewise, during the progress of heel strike, strong pressure may be applied to a portion that overlaps a rearfoot portion in the insole 1, that is, a portion to which the rear electronic element 122 is provided. During an overall gait period, relatively small pressure may be applied to a portion that overlaps a midfoot portion in the insole 1, that is, around the base hole 113.

The guide 114 may be formed in front of the base hole 113, and may have a slope shape that is inclined rearward and downward of the base body 111. The guide 114 may guide the connection line 13 from the top surface to the bottom surface of the base 11 through the base hole 113. Since the guide 114 is in a slope shape that is inclined rearward and downward, the connection line 13 may be bent at a gentle angle. The guide 114 may enhance the durability of the connection line 13 by reducing a bending angle of the connection line 13. The guide 114 may assist a contact point to be easily secured between the connection line 13 and the controller 15.

The electronic element 12 may be provided to the base body 111. For example, the support layer 14 of a flexible material may be provided to the base body 111, and the electronic element 12 may be provided on a top surface or a bottom surface of the support layer 14 or may be embedded in the support layer 14. Also, the electronic element 12 may be directly provided to the base body 111 without using the support layer 14.

The electronic element 12 may apply stimuli to the foot of the user, may measure the pressure applied from the foot of the user, and/or may sense a motion of the foot of the user. For example, the electronic element 12 may include a vibrator, a pressure sensor, a temperature sensor, or an inertial sensor.

For example, in some example embodiments, the electronic element 12 may include the vibrator, for example, an eccentric motor. The vibrator may cause stochastic resonance on the sole of the user. For example, the vibrator may generate vibration noise of a tactile threshold sensible by the sole of the user or less and may provide the vibration noise to the sole of the user. In this case, a tactile signal transferred to the sole of the user is amplified by resonance with the vibration noise and a sense of the sole of the user may become acute.

In some example embodiments, the electronic element 12 may include the pressure sensor, for example, a piezoelectric pressure sensor or a force sensitive resistor (FSR) pressure sensor. The pressure sensor may measure a magnitude of pressure applied from the sole of the user. Information measured by the pressure sensor may be used to analyze a gait posture of the user.

In some example embodiments, the electronic element 12 may include the temperature sensor. The electronic element 12 may measure a temperature of each of the forefoot and the rearfoot of the user.

In some example embodiments, the electronic element 12 may include the inertial sensor. The inertial sensor may measure a magnitude and/or direction of acceleration of each portion of the foot of the user, for example, the forefoot or the rearfoot of the user. Information measured by the inertial sensor may be used to analyze a gait pattern of the user.

In some example embodiments, the electronic element 12 may be provided in plural. Although four electronic elements 12 are illustrated, it is provided as an example. Also, a single electronic element 12 may be configured. The electronic elements 12 may include the front electronic element 121 and the rear electronic element 122.

The front electronic element 121 may include a first front electronic element 121a and a second front electronic element 121b that are arranged in a widthwise direction of the insole 1. The first front electronic element 121a may be arranged at a location that overlaps a forefoot portion toward a little toe of the user based on a direction perpendicular to the insole 1, that is, a location that overlaps an outer side portion of the forefoot portion. The second front electronic element 121b may be arranged at a location that overlaps a forefoot portion toward a big toe of the user, that is, an inner side portion of the forefoot portion. When each of the first front electronic element 121a and the second front electronic element 121b includes a vibrator, the first front electronic element 121a may apply stimuli to the outer side portion of the forefoot of the user and the second front electronic element 121b may apply stimuli to the inner side portion of the forefoot of the user. When each of the first front electronic element 121a and the second front electronic element 121b includes a pressure sensor, the first front electronic element 121a and the second front electronic element 121b may measure pressure applied to an outer side and an inner side of the forefoot of the user. The measured pressure information may be used to sense whether the user is currently performing inversion or performing eversion.

The rear electronic element 122 may include a first rear electronic element 122a and a second rear electronic element 122b that are arranged in a longitudinal direction of the insole 1. The first rear electronic element 122a may be provided relatively rearward relative to the second rear electronic element 122b. When each of the first rear electronic element 122a and the second rear electronic element 122b includes a pressure sensor, a gait state of the user may be further precisely sensed based on pressure information measured by the first rear electronic element 122a and the second rear electronic element 122b. For example, during the progress of heel strike, the second rear electronic element 122b may not sense pressure and the first rear electronic element 122a may sense the pressure. During the progress of mid-stance, a magnitude of pressure sensed by the first rear electronic element 122a and a magnitude of pressure sensed by the second rear electronic element 122b may be approximately similar.

The connection line 13 may be electrically connected to the electronic element 12. The connection line 13 may extend from the electronic element 12 and may pass through the base 11. The connection line 13 may enter the base hole 113 along the guide 114 from the top surface of the base 11. An end of the connection line 13 may be connected to the controller 15 that is provided below the base 11. One end of the connection line 13 may be connected to the electronic element 12 and another end of the connection line 13 may be connected to the controller 15. An access between the electronic element 12 and the controller 15 is enabled through the connection line 13. For example, the connection line 13 may be provided on a top surface or a bottom surface of the support layer 14, or may be embedded in the support layer 14. The connection line 13 may be directly provided to the base body 111 without using the support layer 14.

The support layer 14 may support the electronic element 12 and the connection line 13, and may insert inward into the base protrusion 112. The support layer 14 may be fitted to the base protrusion 112. The support layer 14 may be fastened inside the base protrusion 112 without shaking. For example, a sum of thicknesses of the support layer 14 and the electronic element 12 may be identical to a height of the base protrusion 112 that protrudes upward from an inner space of the base protrusion 112 in the base body 111. For example, the top surface of the electronic element 12 and the top surface of the base protrusion 112 may be formed at the same height. The support layer 14 may include a layer body 141 and a slope part (or, alternatively, a ramp) 142.

The layer body 141 may be provided on the top surface of the base body 111. The layer body 141 may support the electronic element 12 and/or the connection line 13. The layer body 141 may be formed of, for example, a flexible film.

The slope part 142 may be formed in a central portion of the layer body 141 and be bent downward relative to the layer body 141 and thereby provided to the guide 114. The slope part 142 may guide the connection line 13 to the controller 15. The slope part 142 may be in a slope shape that is inclined downward and rearward from an upper portion of the layer body 141.

For example, the slope part 142 may be formed by folding and bending a portion of the support layer 14 configured as a single layer and the layer body 141 may be formed using a remaining portion of the support layer 14.

The controller 15 may be electrically connected to the electronic element 12 and may control the electronic element 12. For example, when the electronic element 12 includes a vibrator, the controller 15 may adjust a frequency and/or an amplitude of the electronic element 12. The controller 15 may receive information from the electronic element 12. For example, when the electronic element 12 includes a pressure sensor or an inertial sensor, the controller 15 may receive information sensed at the electronic element 12.

The controller 15 may be mounted to the insole 1. For example, the controller 15 may insert into an underside of the base 11. According to the above structure, the midsole 2 does not require a space for receiving the controller 15. That is, the midsole 2 and the upper 3 may be manufactured in a manner similar to a general shoe manufacturing process and may couple with each other regardless of whether the controller 15 is provided. That is, the shoe manufacturing process and a process of manufacturing the base 11 including an electronic part may be separately performed. For example, when the upper 3 includes the upper sole 32, the upper sole 32 may be attached on a top surface of the midsole 2. As another example, when the upper 3 does not include the upper sole 32, the upper 3 may couple with the midsole 2 along the edge of the midsole 2. The midsole 2 and the upper 3 do not require a space for receiving the controller 15 and assembly order thereof is not affected by the controller 15. Accordingly, the shoe 100 may be produced on a large scale through a simple automation process without causing damage to various types of electronic parts that are relatively expensive and have low durability or without causing disconnection of the connection line. The controller 15 may include a controller body 151, a controller protrusion 152, an access port 153, a power unit 158, and processing circuitry 159. In some example embodiments, the controller 15 may further include a memory (not shown).

The processing circuitry 159 may include hardware including logic circuits, a hardware/software combination such as a processor executing software; or a combination thereof. For example, the processing circuitry may include, but is not limited to, a central processing unit (CPU), an arithmetic logic unit (ALU), a digital signal processor, a microcomputer, a field programmable gate array (FPGA), a System-on-Chip (SoC) a programmable logic unit, a microprocessor, or an application-specific integrated circuit (ASIC), etc.

The processing circuitry 159 may execute instructions stored in the memory to configure the processing circuitry 159 as special purpose processing circuitry to control the electronic element 12 in response to a control signal input through the interface 4 or wireless communication.

The controller body 151 may insert into the base 11 in a first direction. For example, the first direction may be a +z-axial direction from an underside of the base 11 toward an upper side of the base 11. The controller body 151 may include the power unit 158 and/or the processing circuitry 159. The controller body 151 may include controller coupling holes 151a and 151b for coupling with the insert 16. For example, the controller coupling holes 151a and 151b may include the first controller coupling hole 151a and the second controller coupling hole 151b that are provided to face each other based on the access port 153.

The controller protrusion 152 may extend rearward from the controller body 151. The controller protrusion 152 may insert into the base 11 in a second direction perpendicular to the first direction. Here, the second direction may be a −x-axial direction from forward of the base 11 toward rearward of the base 11. Since the second direction is orthogonal to the first direction, it is possible to inhibit (or, alternatively, prevent) the controller body 151 from being separated downward during a process of mounting the controller body 151 to the base 11. The controller protrusion 152 may provide a temporary fastening state by making one end of the controller 15 be locked by the base 11 before mounting the controller body 151. A front portion of the controller body 151 couples with the insert 16 and the controller protrusion 152 that extends rearward from the controller body 151 inserts into the base 11. Therefore, a state in which the controller 15 is inserted into the base 11 may be stably maintained while the user is walking. For example, although the central portion of the base 11 is deformed due to a push-off motion of the user, the controller 15 may not be separated from the base 11 since the controller 15 is coupled with the insert 16 of a rigid material. Also, although the rear portion of the base 11 is deformed due to a heel-strike motion of the user, the controller 15 may not be separated from the base 11 since the controller protrusion 152 is inserted into the base 11.

The access port 153 may be provided on a top surface of the controller body 151. The access port 153 may be connected to the connection line 13 that passes through the base hole 113. The access port 153 may be a member, for example, a pogo pin, which is elastically deformable in a direction in which the access port 153 is connected to the connection line 13. According to the above, a stable electrical contact point may be provided while the user is walking.

The power unit 158 may supply power to the electronic element 12. The power unit 158 may be charged with power supplied from an outside through the interface 4, or may be wirelessly charged.

The insert 16 may be provided inside the base 11 and may be formed of a more rigid material than that of the base 11. For example, the insert 16 may be integrally formed with the base 11 inside the base 11 by forming the base 11 through a resin foaming process in a state in which the insert 16 is provided in a molding frame for forming the base 11. The insert 16 may be present adjacent to the base hole 113 and may overlap the controller 15 based on the direction perpendicular to the insole 1. The insert 16 may include insert coupling holes 16a and 16b for coupling with the controller 15. The insert coupling hole 16a, 16b may include a screw thread inward. The insert coupling holes 16a and 16b may include the first insert coupling hole 16a corresponding to the first controller coupling hole 151a and the second insert coupling hole 16b corresponding to the second controller coupling hole 151b. Although FIG. 3 illustrates an example embodiment of fastening a front end of the controller 15 using a single insert 16, it is provided as an example only. A plurality of inserts 16 may be provided and used to fasten another portion of the controller 15. Also, the insert 16 may be in a different shape to make it possible to fasten a plurality of portions of the controller 15.

The cover 19 may be provided on the top surface of the base 11 to cover the electronic element 12 such that the electronic element 12 does not make a direct contact with the foot of the user. The shape of the cover 19 may be approximately similar to the shape of the base 11. The cover 19 may mostly overlap the base 11 based on the direction perpendicular to the insole 1. The cover 19 may be in a shape of a cover sole 19a and a cover wing 19b, where the cover wing 19b is configured to protrude upward from a rear edge portion of the cover sole 19a. The cover wing 19b may stably support the rearfoot of the user by surrounding a rear portion and a side portion of the rearfoot of the user. For example, an electronic part may not be provided in the cover 19. According to the above structure, the user may clean or replace the cover 19 by separating only the cover 19 from the shoe 100. Also, without a need to modify a structure of the base 11 that includes various types of electronic parts, it is possible to provide the cover 19 in a shape that is customized for various shapes of the foot of the user. Accordingly, it is possible to save the overall cost and efforts for manufacturing the shoe 100.

The coupling members 81 and 82 may be used to couple the controller 15 and the insert 16. For example, the coupling members 81 and 82 may be bolts that are screwable to the controller 15 and the insert 16.

The midsole 2 may form at least a portion of a lower external appearance of the shoe 100. The midsole 2 becomes thicker with getting closer to a rear portion. Therefore, a front portion of the midsole 2 configured to support the forefoot of the user may have a thickness less than that of a portion configured to support a heel of the user. The midsole 2 may include a midsole body 21 and a plurality of midsole grooves 22. If necessary, the midsole 2 may include an outsole (not shown) formed on a bottom surface of the midsole body 21 and formed of a more rigid material than that of the midsole body 21.

The midsole body 21 may support the insole 1. The upper 3 may be provided above the midsole body 21. The midsole body 21 may be formed of, for example, phylon, cushlon, ethylene-vinyl acetate copolymer (EVA), or solyte.

A plurality of midsole grooves 22 may be formed in a direction, for example, a y-axial direction, which intersects a longitudinal (x-axial direction) of the midsole body 21 and may be provided at a location at which the midsole grooves 22 do not overlap the electronic element 12. For example, the midsole groove 22 may be provided in front of the electronic element 12. The plurality of midsole grooves 22 may guide a location at which the midsole body 21 bends. The plurality of midsole grooves 22 may assist the midsole body 21 to bend at a nonoverlapping location with the electronic element 12, thereby reducing a risk that the electronic element 12 may be damaged. For example, referring to FIG. 2, the midsole groove 22 may be recessed from the top surface of the midsole body 21. For example, the plurality of midsole grooves 22 may be formed in parallel.

As discussed above, in some example embodiments, the midsole 2 may include a plurality of midsole grooves 22 therein. However, example embodiments are not limited thereto. For example, in some example embodiments, in addition to or in lieu of the midsole grooves 22, the insole 1 may include grooves in one or more of the insole body 11 and/or the cover 19 to urge the insole 1 to flex at a location that does not correspond to the electronic element 12.

The upper 3 may form an upper external appearance of the shoe 100 and may wrap around the foot of the user. The upper 3 may include an upper body 31 and an upper sole 32 configured to contact the top surface of the midsole body 21. The upper body 31 may include an upper hole 31a through which the interface 4 accesses the controller 15. The interface 4 may be connected to the controller 15 by passing through the upper hole 31a. The upper hole 31a may be formed on a rear surface of the upper body 31.

The interface 4 may be electrically connected to the controller 15. For example, a portion of the interface 4 may be provided at the rear of the midsole 2 and externally exposed and a remaining portion of the interface 4 may be connected to the controller 15. For example, the interface 4 may include an input unit, for example, a button, configured to receive a control signal from the user and may transmit the control signal to the processing circuitry 159. For example, the interface 4 may be supplied with power from an outside and may supply the power to the power unit 158.

Figure 5:
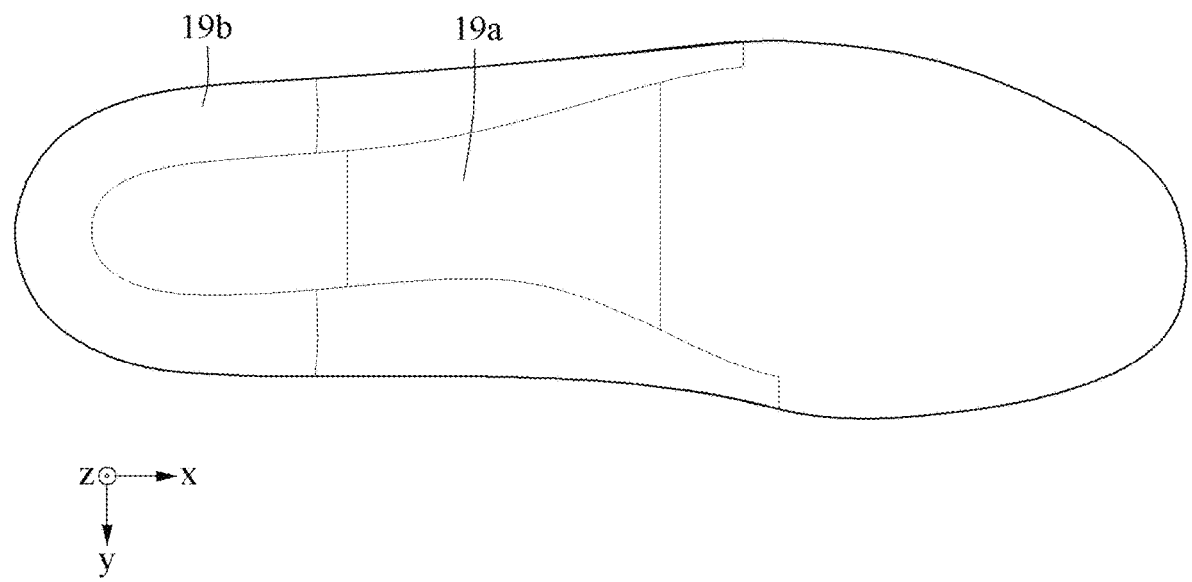
FIG. 5 is a top view of a cover according to at least one example embodiment.
Figure 6:
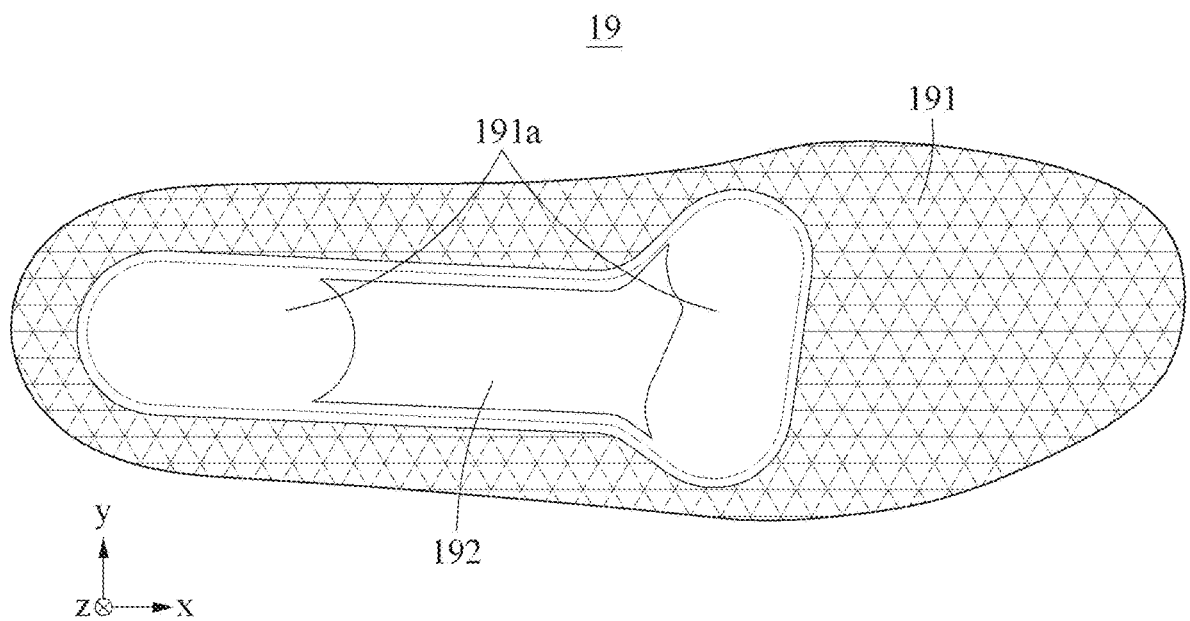
FIG. 6 is a bottom view of a cover according to at least one example embodiment.
Figure 7:
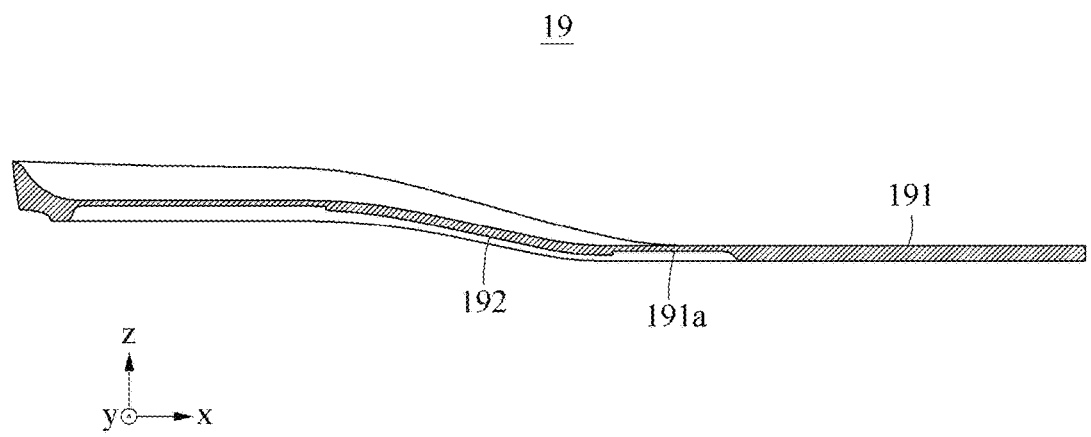
FIG. 7 is a cross-sectional view of a cover according to at least one example embodiment.
Figure 8:
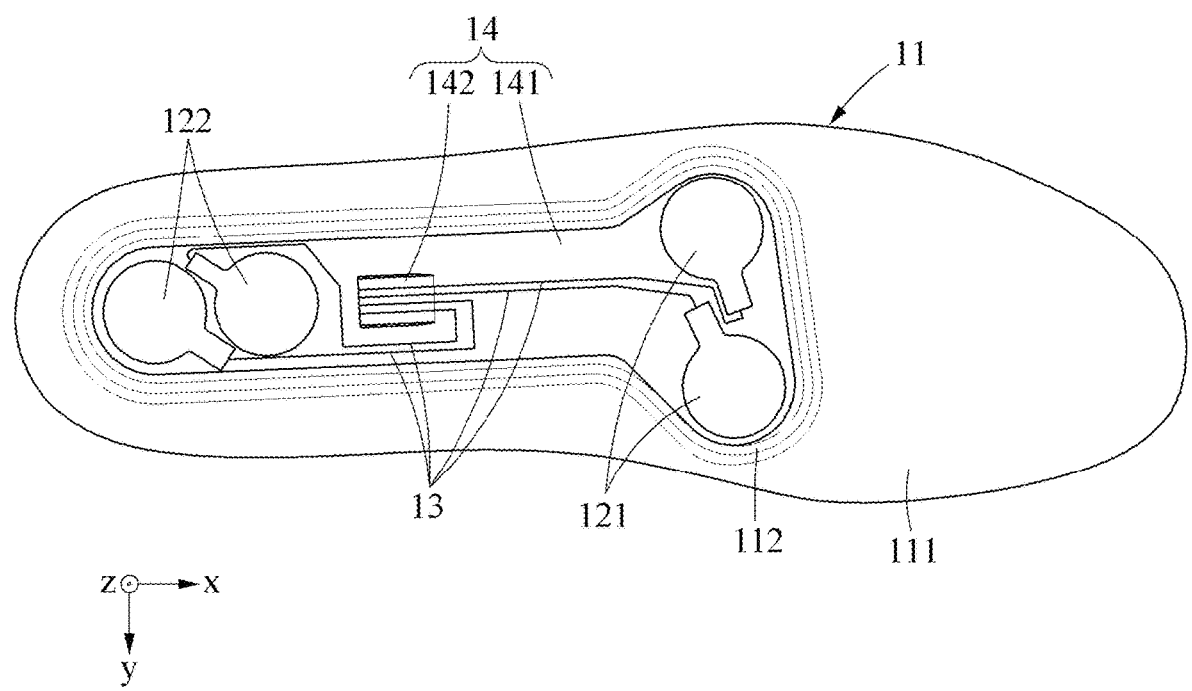
FIG. 8 is a top view illustrating a base, an electronic element, a connection line, and a support layer according to at least one example embodiment.
Figure 9:
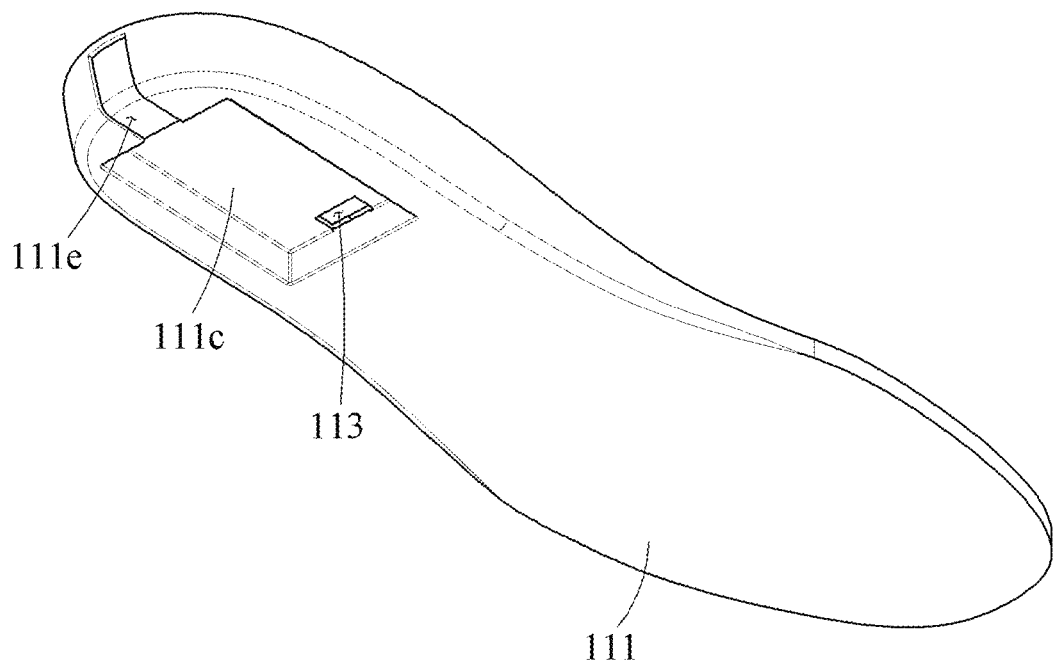
FIG. 9 is a perspective view of a base according to at least one example embodiment.
Figure 10:
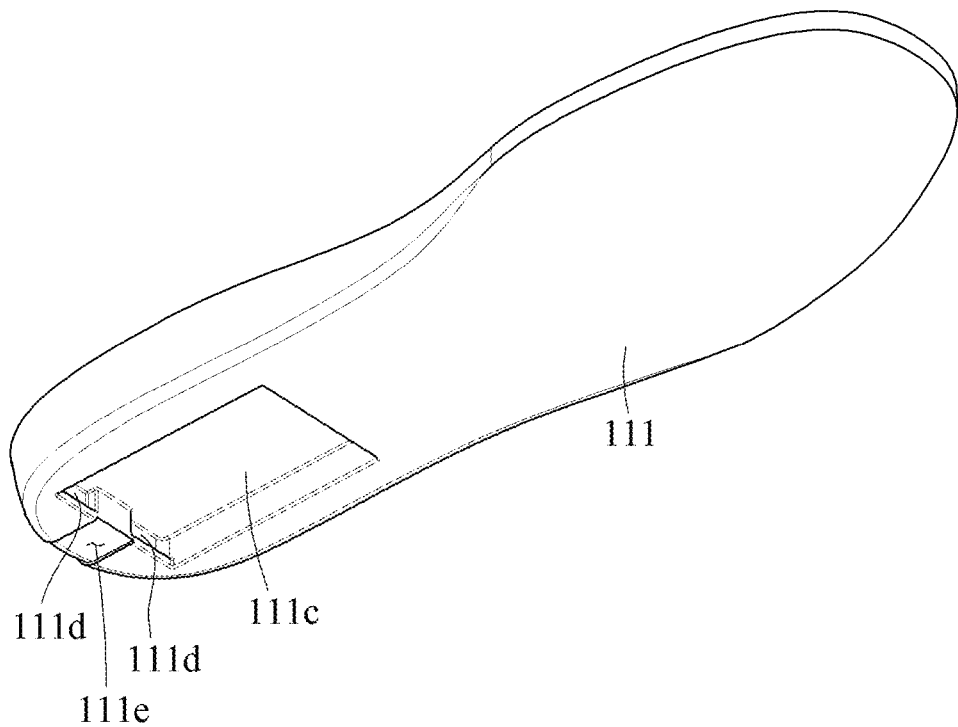
FIG. 10 is a perspective view of the base of FIG. 9 observed at a different angle.

FIG. 5 is a top view of a cover according to at least one example embodiment, FIG. 6 is a bottom view of a cover according to at least one example embodiment, FIG. 7 is a cross-sectional view of a cover according to at least one example embodiment, FIG. 8 is a top view illustrating a base, an electronic element, a connection line, and a support layer according to at least one example embodiment, FIG. 9 is a perspective view of a base according to at least one example embodiment, and FIG. 10 is a perspective view of the base of FIG. 9 observed at a different angle.

Referring to FIGS. 5 to 10, the cover 19 may be separable from the base 11. The cover 19 may have a shape that includes the cover sole 19a and the cover wing 19b.

The cover 19 may include a cover body 191 including a cover groove 191a and a cover protrusion 192 configured to protrude from the cover body 191.

The cover groove 191a may be in a shape that receives the electronic element 12 and the support layer 14. For example, the front electronic element 121 may be received in a front portion of the cover groove 191a and the rear electronic element 122 may be received in a rear portion of the cover groove 191a. The front portion of the cover groove 191a may be relatively wider than the rear portion of the cover groove 191a. A depth of the cover groove 191a that is recessed from a bottom surface of the cover body 191 may be approximately identical to a sum of thicknesses of the support layer 14 and the electronic element 12. When the cover 19 covers the base 11, the electronic element 12 may be in contact with a bottom surface of the cover groove 191a. The base protrusion 112 may be fitted to the cover groove 191a. The cover groove 191a may be in a shape corresponding to a shape of the base protrusion 112.

However, example embodiments are not limited to the cover 19 being connected to the base 11 via only the protrusion 112 connected to the groove 191a. For example, in other example embodiments, the cover 19 may be connected to the base 11 by various fastening means. For example, in some example embodiments, the cover 19 and the base body 111 be connected via a hook-and-loop fastener. In some example embodiments, the hook-and-loop fastener may be used in addition to the protrusion 112 and the groove 191a to provide additional fixing force between the cover 19 and the base 11. While in other example embodiments, the hook-and-loop fastener may be used in lieu of the protrusion 112 and the groove 191a to fix the cover 19 to the base 11.

The cover protrusion 192 may press the support layer 14. The cover protrusion 192 may press a portion that does not support the electronic element 12 in the support layer 14. For example, the cover protrusion 192 may protrude from the cover body 191 by a length corresponding to a thickness of the electronic element 12. When the cover 19 covers the base 11, the support layer 14 may be in contact with the cover protrusion 192. While the user is walking, the cover protrusion 192 may assist a central portion of the support layer 14 to not shake vertically.

The support layer 14 may be fitted inside the base protrusion 112. For example, an edge portion of the layer body 141 may maintain a contact state with an inner wall of the base protrusion 112. A horizontal shaking of the front electronic element 121 and the rear electronic element 122 may be limited.

If necessary, the support layer 14 may be separated from the base 11 and may be repaired and/or replaced. For example, various types of support layers 14 may support various types of electronic elements 12. For example, the support layer 14 may support one of an electronic element including an eccentric motor, an electronic element including a pressure sensor, and an electronic element including an inertial sensor. The user may selectively provide the support layer 14 supporting a desired electronic element to the base 11.

The base body 111 may include a base main groove 111c recessed from a bottom surface of the base body 111, a base auxiliary groove 111d that is recessed from one side surface of the base main groove 111c toward the rear portion of the base 11, and a line receiving groove 111e.

The base main groove 111c may receive the controller body 151 of FIG. 3, and the base auxiliary groove 111d may receive the controller protrusion 152 of FIG. 3. The user may insert the controller protrusion 152 into the base auxiliary groove 111d with titling the controller body 151 and may lift the controller body 151 to be fully inserted into the base main groove 111c.

Figure 13:
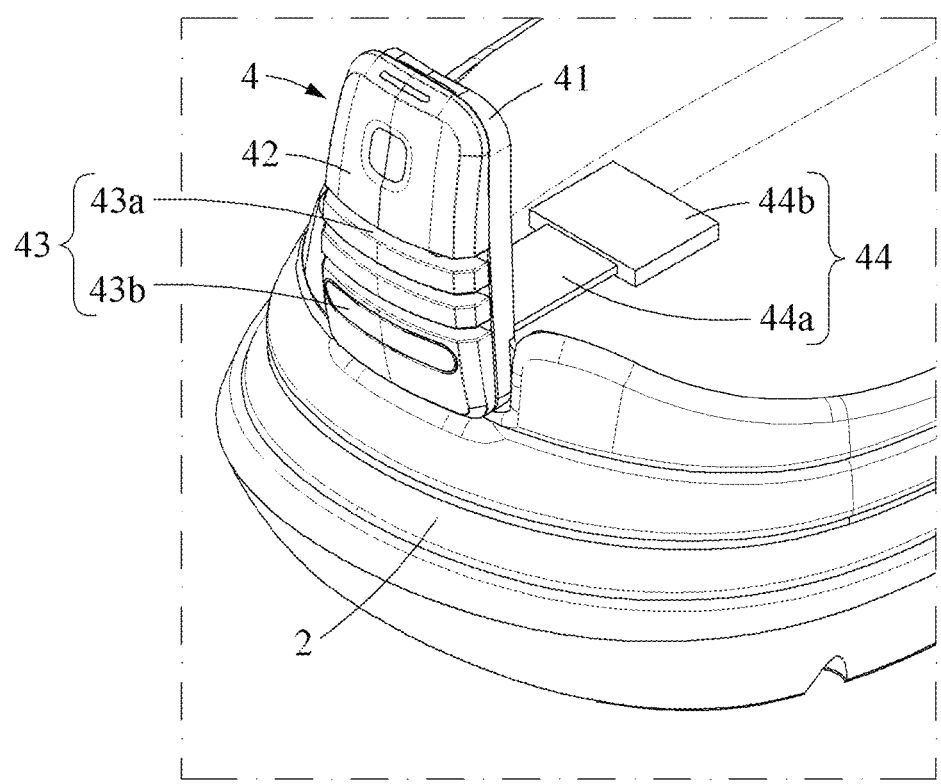
FIG. 13 is a perspective view illustrating a midsole and an interface according to at least one example embodiment.

The line receiving groove 111e may receive a power line 44a of FIG. 13. The line receiving groove 111e may inhibit (or, alternatively, prevent) aging of the power line 44a by friction with the insole 1 during a walking process of the user and may also enable a stable connection between the controller 15 and the interface 4. For example, the line receiving groove 111e may be formed across the rear surface and the bottom surface of the base body 111. The line receiving groove 111e may be in a shape that communicates with the base main groove 111c.

Figure 11:
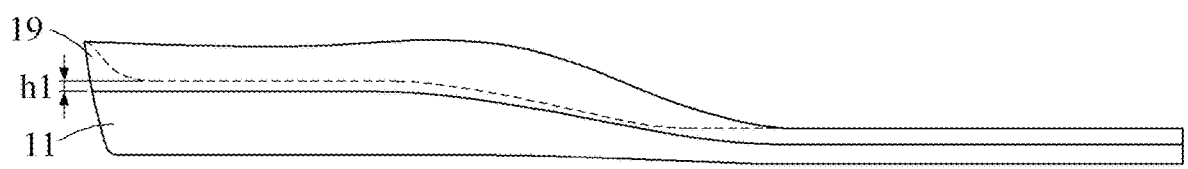
FIG. 11 is a side view illustrating an example of replacing a cover according to at least one example embodiment.
Figure 11:
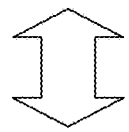
Figure 11:
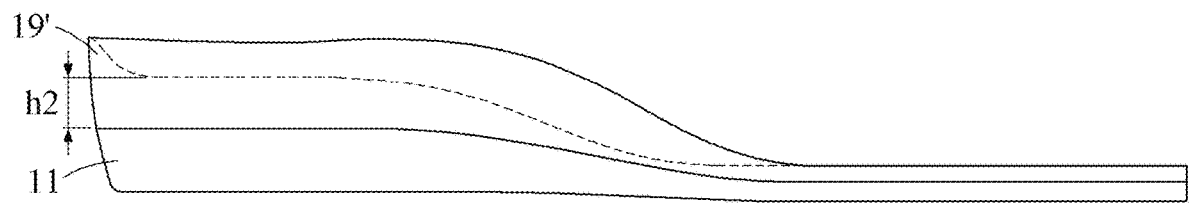

FIG. 11 is a side view illustrating an example of replacing a cover according to at least one example embodiment.

Referring to FIG. 11, the cover 19 may be replaced while the electronic element 12 remains mounted to the base 11. The user may use the cover 19 that is customized for the user in various ways such as, for example, height, rigidity and/or shape. For example, the user may replace the cover 19 with a height h1 with a cover 19' with a height h2 with respect to a portion that supports the rearfoot of the user.

Figure 12:
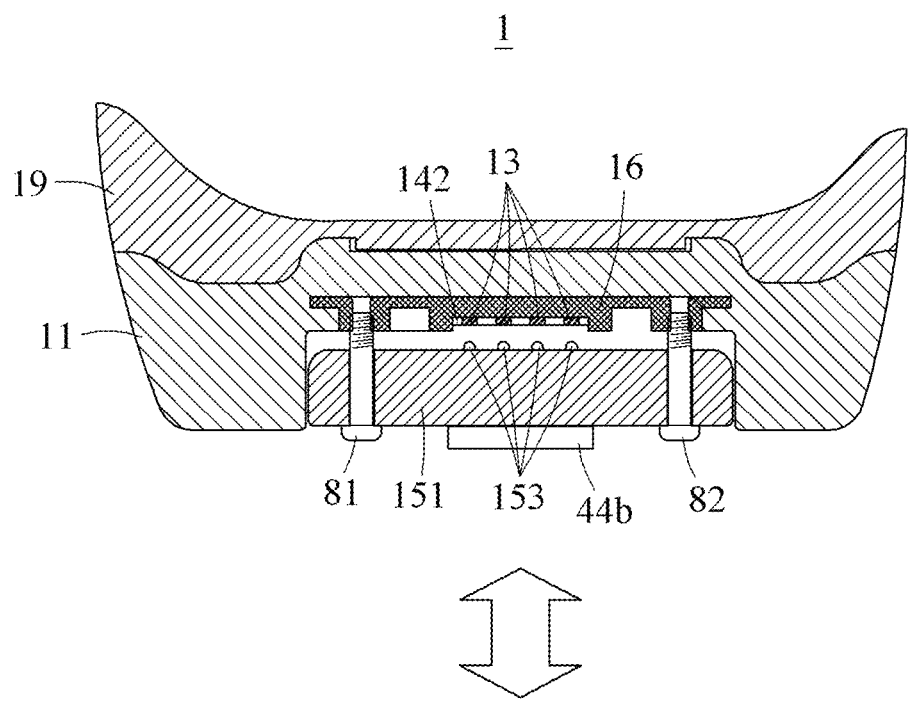
FIG. 12 is a cross-sectional view of an insole according to at least one example embodiment.
Figure 12:
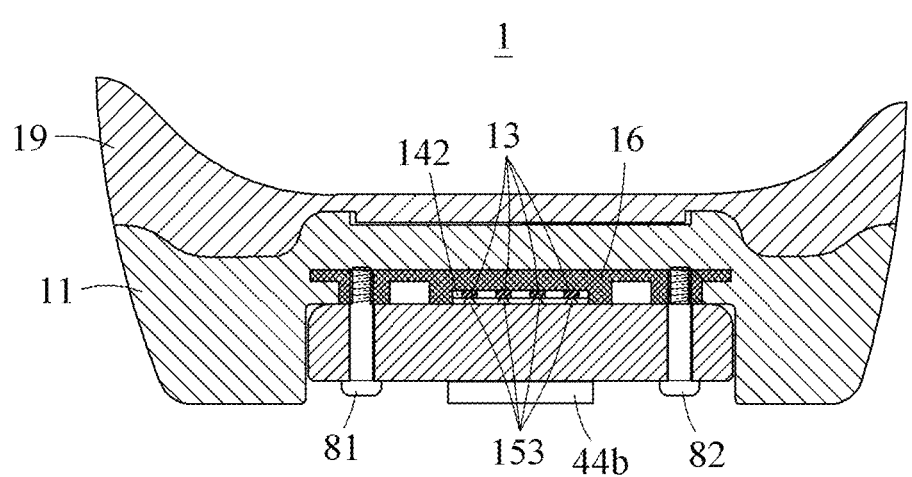
Figure 14:
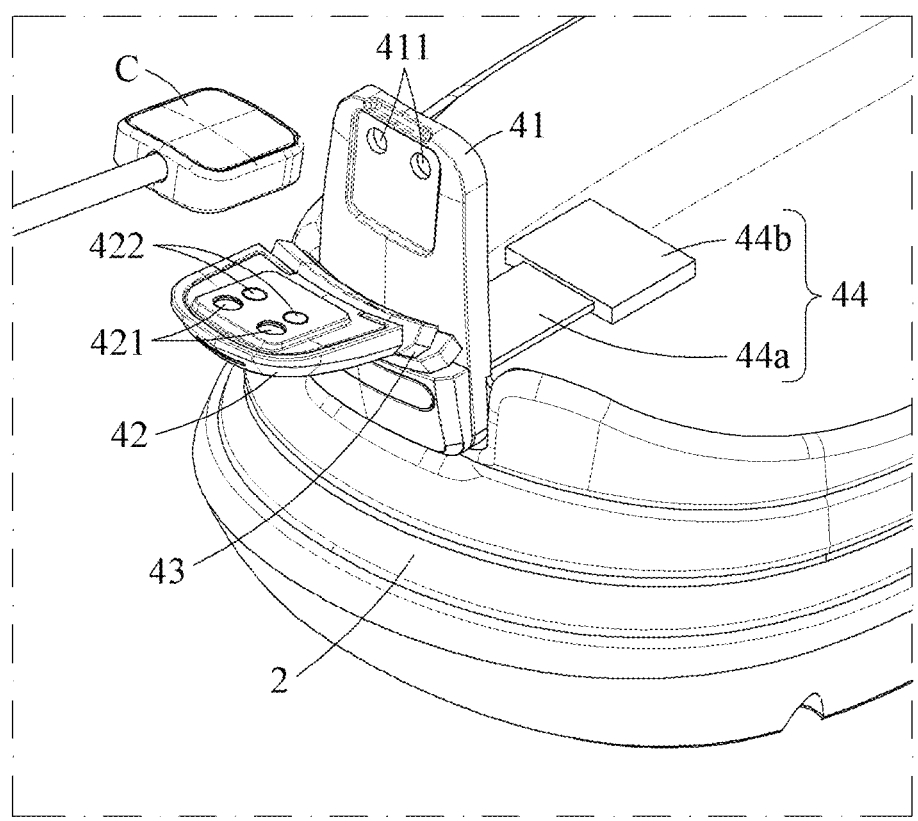
FIG. 14 is a perspective view illustrating a state in which an interface cover is separated from an interface body according to at least one example embodiment.

FIG. 12 is a cross-sectional view of an insole according to at least one example embodiment, FIG. 13 is a perspective view illustrating a midsole and an interface according to at least one example embodiment, and FIG. 14 is a perspective view illustrating a state in which an interface cover is separated from an interface body according to at least one example embodiment.

Referring to FIGS. 12 to 14, the interface 4 may include an interface body 41, an interface cover 42, a connecting portion 43, and a connector 44.

The interface body 41 may be fastened to the midsole 2. For example, the interface body 41 may be fastened to a rear edge portion of the midsole 2. The interface body 41 may be formed of a more rigid material than that of the upper 3 of FIG. 1 and may act as a back counter of the shoe 100. The interface body 41 may include a body magnet 411 configured to apply a magnetic force to the interface cover 42. A plurality of body magnets 411 may be provided.

The interface cover 42 may be detachably provided to the interface body 41. The interface cover 42 may include a cover magnet 421 configured to face the body magnet 411 with a polarity opposite to that of the body magnet 411 and a power terminal 422 configured to receive power that is supplied to the power unit 158 of FIG. 4. A plurality of cover magnets 421 may be provided. An external charging device C may be connected to the power terminal 422.

An upper end 43a of the connecting portion 43 may be connected to the interface cover 42 and a lower end 43b of the connecting portion 43 may be fastened to the interface body 41. Although the interface cover 42 is separated from the interface body 41, the connecting portion 43 may assist the interface cover 42 not to be separated from the shoe 100. The user may separate the interface cover 42 from the interface body 41 by pulling an upper end of the interface cover 42. For example, the connecting portion 43 may be formed of an elastic material.

The connector 44 may pass through the upper hole 31a of the upper 3 of FIG. 2 and may connect the power terminal 422 and the controller 15 of FIG. 3. The connector 44 may include the power line 44a configured to pass through the upper 3 and a connector terminal 44b provided at an end of the power line 44a and configured to connect to the controller 15.

The power line 44a may extend along the rear surface and the bottom surface of the base 11. For example, the power line 44a may include a flexible material, such as a fabric material. According to the above structure, although some clearance of the controller 15 occurs in the shoe 100 while the user is walking, the power line 44a may tolerate the clearance, thereby reducing a risk of disconnection. That is, it is possible to enhance the product durability compared to a case in which the connector 44 is in an overall rigid structure.

The connector terminal 44b may be provided to be detachable from a bottom surface of the controller 15. According to the above structure, if there is a need to repair or replace electronic parts installed on the base 11, the entire base 11 may be easily separated from the shoe 100 by separating the connector terminal 44b from the controller 15.

The connection line 13 may be guided to the underside of the base 11 by the slope part 142. When the coupling members 81 and 82 couple the controller body 151 and the insert 16, the access port 153 may be in contact with the connection line 13. For example, the controller body 151 may include an elastic body (not shown) configured to provide an upward elastic force to the access port 153.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An insole comprising:
    a base having a base hole therein extending from a top surface of the base to a bottom surface of the base;
    an electronic element provided to the base;
    a controller insertable into the bottom surface of the base;
    a connection line extending from the electronic element and passing through the base hole;
    a cover configured to detachably connect to the top surface of the base such that the cover covers the electronic element when the cover is connected to the base; and
    a support layer configured to support the electronic element and the connection line,
    wherein the base comprises:
        a base body configured to support the electronic element, the base body has the base hole passing therethrough such that a front sidewall of the base hole is sloped rearward and downward from the base body to form a guide; and
        a base protrusion protruding from the base body, the base protrusion configured to connect to the cover such that the electronic element supported by the base body is surrounded by the base protrusion,
    wherein the support layer is configured to be fitted to an inside of the base protrusion, and the support layer comprises:
        a layer body configured to rest on the top surface of the base, the connection line extending along a top surface of the layer body; and
        a ramp formed on a central portion of the layer body, the ramp having a slope corresponding to a slope of the guide such that the connection line runs along the ramp and passes through the base.

2. The insole of claim 1, wherein the electronic element comprises:
    a plurality of electronic devices including,
        a front electronic device configured to overlap a forefoot of a user based on a direction perpendicular to the base; and
        a rear electronic device configured to overlap a rear foot of the user based on the direction perpendicular to the base.

3. The insole of claim 2, wherein the base hole in the base body is at a position corresponding to a location between the front electronic device and the rear electronic device.

4. The insole of claim 1, wherein the cover comprises:
a cover body including a cover groove configured to receive the base protrusion; and
a cover protrusion configured to protrude from the cover body and to press against the support layer.

5. The insole of claim 1, wherein
the electronic element is provided to the top surface the base, and
the controller is insertable into the bottom surface of the base such that the controller is provided on an opposite side of the base with respect to the electronic element.

6. The insole of claim 1, wherein the controller comprises:
a controller body having a controller protrusion extending rearward from the controller body, such that the controller is insertable into the base by inserting the controller in a main groove in the base such that the controller protrusion penetrates an auxiliary groove within the main groove, the auxiliary groove recessed from one side surface of the main groove toward a rear portion of the base.

7. The insole of claim 5, further comprising:
an insert in the base, the insert including a more rigid material than that of the base, wherein
the controller and the insert are configured to be combinable in a state in which the connection line is between the controller and the insert.

8. The insole of claim 1, wherein the electronic element comprises:
at least one electronic device including a vibrator, a pressure sensor, a temperature sensor, or an inertial sensor.

9. A shoe comprising:
a midsole;
an upper on a top surface of the midsole; and
an insole including,
a base insertable into the upper, the base having a base hole therein extending from a top surface of the base to a bottom surface of the base,
an electronic element provided to the base,
a controller insertable into the bottom surface of the base,
a connection line extending from the electronic element and passing through the base hole,
a cover configured to detachably connect to the top surface of the base such that the cover covers the electronic element when the cover is connected to the base; and
a support layer configured to support the electronic element and the connection line,
wherein the base comprises:
a base body configured to support the electronic element, the base body has the base hole passing therethrough such that a front sidewall of the base hole is sloped rearward and downward from the base body to form a guide; and
a base protrusion protruding from the base body, the base protrusion configured to connect to the cover such that the electronic element supported by the base body is surrounded by the base protrusion,
wherein the support layer is configured to be fitted to an inside of the base protrusion, and the support layer comprises:
a layer body configured to rest on the top surface of the base, the connection line extending along a top surface of the layer body; and
a ramp formed on a central portion of the layer body, the ramp having a slope corresponding to a slope of the guide such that the connection line runs along the ramp and passes through the base.

10. The shoe of claim 9, wherein
the electronic element is provided to the top surface the base, and
the controller is insertable into the bottom surface of the base such that the controller is provided on an opposite side of the base with respect to the electronic element.

11. The shoe of claim 9, further comprising:
an interface attached to an exterior of one of the upper and the midsole, the interface configured to connect to the controller.

12. The shoe of claim 11, wherein the interface comprises:
an interface body configured to fasten to the midsole;
an interface cover including a power terminal, the interface cover detachably connected to the interface body; and
a connector configured to pass through the upper and connect the power terminal to the controller.

13. The shoe of claim 12, wherein
the interface body includes a body magnet having a first polarity, and
the interface cover further includes a cover magnet configured to face the body magnet, the cover magnet having a second polarity opposite the first polarity.

14. The shoe of claim 9, wherein the midsole comprises:
a midsole body configured to support the insole; and
a plurality of midsole grooves recessed in front portion of a top surface thereof and extending in a direction intersecting a longitudinal direction of the midsole body such that the plurality of midsole grooves are in front of the electronic element.

* * * * *